United States Patent [19]

Ribier et al.

[11] Patent Number: 5,741,518
[45] Date of Patent: Apr. 21, 1998

[54] COMPOSITION COMPOSED OF AN AQUEOUS DISPERSION OF STABILIZED VESICLES OF NONIONIC AMPHIPHILIC LIPIDS

[75] Inventors: Alain Ribier; Jean-Thierry Simonnet; Rose-Marie Handjani, all of Paris; Nadia Terren, Chevilly-Larue, all of France

[73] Assignee: L'Oreal, Paris, France

[21] Appl. No.: 698,658

[22] Filed: Aug. 16, 1996

Related U.S. Application Data

[63] Continuation of Ser. No. 473,360, Jun. 7, 1995, abandoned.

[30] Foreign Application Priority Data

Aug. 3, 1992 [FR] France ............................ 92 09603
Oct. 15, 1992 [FR] France ............................ 92 12343

[51] Int. Cl.$^6$ ............................................ A61K 9/127
[52] U.S. Cl. ...................... 424/450; 424/401; 428/402.2
[58] Field of Search ............................ 424/400, 401; 428/402.2; 264/4.1, 4.3, 4.6

[56] References Cited

U.S. PATENT DOCUMENTS

| 4,670,185 | 6/1987 | Fujiwara | 252/311 |
| 4,832,944 | 5/1989 | Socci | 424/61 |
| 5,229,104 | 7/1993 | Sottery | 424/59 |
| 5,246,693 | 9/1993 | Grollier | 424/70 |
| 5,290,562 | 3/1994 | Meybeck | 424/450 |

FOREIGN PATENT DOCUMENTS

| 0319638 | 6/1989 | European Pat. Off. . |
| 0433131 | 6/1991 | European Pat. Off. . |
| 2552666 | 4/1985 | France . |
| 2151203 | 7/1985 | United Kingdom . |
| 9006747 | 6/1990 | WIPO . |

OTHER PUBLICATIONS

French Search Report—FR 92 09603.
French Search Report—FR 92 12343.

*Primary Examiner*—Gollamudi S. Kishore
*Attorney, Agent, or Firm*—Nixon & Vanderhye P.C.

[57] ABSTRACT

The vesicles are prepared from a lipid phase containing a mixture of nonionic amphiphilic lipids consisting of a mixture of esters of at least one polyol chosen from the group composed of polyethylene glycol containing from 1 to 60 ethylene oxide units, sorbitan, sorbitan bearing 2 to 60 ethylene oxide units, glycerol bearing 2 to 30 ethylene oxide units, polyglycerols containing 2 to 15 glycerol units, sucroses, and glucoses bearing 2 to 30 ethylene oxide units and of at least one fatty acid containing a saturated or unsaturated, linear or branched $C_5$–$C_{17}$ alkyl chain, the number of alkyl chains per polyol group being between 1 and 10, the mixture being stabilized with ionic amphiphilic lipid or lipids chosen from the group composed of those which impart a pH of between 5.5 and 7.5 to the dispersion.

13 Claims, No Drawings

COMPOSITION COMPOSED OF AN AQUEOUS DISPERSION OF STABILIZED VESICLES OF NONIONIC AMPHIPHILIC LIPIDS

This is a continuation of application Ser. No. 08/473,360, filed Jun. 7, 1995 abandoned.

The present invention relates to a composition composed of an aqueous dispersion of vesicles of certain nonionic amphiphilic lipids, which are stabilized and do not degrade during storage. This composition is especially advantageous in cosmetics and dermopharmacy.

It is known that certain amphiphilic lipids possess the property of forming mesomorphic phases, the state of organization of which is intermediate between the crystalline state and the liquid state, and that some of these are capable of swelling in the presence of an aqueous solution to form a lamellar phase and then, after agitation, to form vesicles or spherules dispersed in an aqueous phase. These vesicles are composed of a membrane consisting of substantially concentric lamellae containing one or more multimolecular layers, preferably bimolecular, encapsulating an aqueous phase.

The abovementioned vesicles may be prepared by many processes. According to a first process, which is, for example, described by Bangham et al. (J. Mol. Bio., 13, 1965—pages 238 to 262), the lipid phase is dissolved in a volatile solvent, a thin film of lipid phase is formed on the walls of a flask by evaporation of the solvent, the phase to be encapsulated is introduced onto the lipid film and the mixture is agitated mechanically until the dispersion of vesicles having the desired size is obtained; an aqueous dispersion of vesicles encapsulating an aqueous phase is thereby obtained, the encapsulated aqueous phase and the aqueous dispersion phase being identical. According to a second, so-called "lipid co-melting" process, described, for example, in FR-A-2,315,991, the lipid phase is prepared by mixing the amphiphilic lipid or lipids and the possible additives at a temperature at which the mixture is molten, if the mixture is not liquid at room temperature; a lamellar phase is formed by introduction of the aqueous phase to be encapsulated; the lamellar phase is then dispersed in the form of vesicles, using an ultradisperser, a homogenizer or ultrasound, in an aqueous dispersion phase. In a variant of this process, the formation of the lamellar phase does not constitute a separate stage of the process. The vesicles obtained by these two processes are generally of the "multilamellate" type. To obtain vesicles of the "monolamellate" type, the teaching of FR-A-2,543,018 may be used.

Irrespective of the process used, the vesicles are obtained in the form of a dispersion in an aqueous phase.

In a known manner, vesicles of amphiphilic lipids can contain cosmetic or pharmaceutical active agents, either in the encapsulated aqueous phase if the said active agents are water-soluble, or in the lipid membrane if they are fat-soluble. Active agents may also be present in the aqueous dispersion phase.

The amphiphilic lipids used for obtaining the vesicles are lipids of the general formula:

X—Y in which formula X represents a hydrophilic group and Y represents a lipophilic group. The amphiphilic lipids can be ionic lipids for which the group X is ionic, or nonionic lipids for which the group X is nonionic.

In a known manner, for the manufacture of vesicles, it is possible to use mixtures of ionic amphiphilic lipids, mixtures of nonionic amphiphilic lipids and mixtures of these two types of lipids.

The proposal has been made, for example, in FR-A 2,315,991, to prepare the vesicles consisting of polyol esters, oxyethylenated or otherwise, from nonionic amphiphilic lipids. The vesicles prepared with the said esters are advantageous in cosmetics and dermopharmacy since they are biodegradable in and on the skin. However, they possess a major drawback: in the presence of water, a hydrolysis of the ester groups in the lipid membrane is observed, this hydrolysis phenomenon being especially extensive when the pH diverges from a value close to neutrality. To remedy this drawback, it has been proposed to introduce a saline buffer solution maintaining the pH at a value between 6 and 7, and preferably in the region of 6.5, into the aqueous phase of dispersion of the vesicles. However, the introduction of saline buffers into compositions used in cosmetics or in dermopharmacy possesses many drawbacks. Saline buffers are incompatible with many additives or active agents commonly used in cosmetics; in particular, they lower the viscosity of compositions containing an anionic gelling agent such as the vinylcarboxylic mixtures marketed by the company "Goodrich" under the name "Carbopol"; they also cause precipitation of proteins. The presence of a saline buffer reduces the electrical charge (zeta potential) of the vesicles, thereby bringing about their flocculation. Furthermore, the presence of the said saline buffer causes a strong corrosion of metals, especially steels, constituting the surfaces of the homogenizers used for the manufacture of the vesicles. Lastly, cosmetic compositions containing a saline buffer impart a rougher feel after application to the skin.

According to the present invention, a means has been found which enables dispersions in which the vesicles are stable in water to be obtained with certain polyol esters; these dispersions can consequently be stored and used for the preparation of cosmetic or dermopharmaceutical compositions without the need to introduce a saline buffer.

According to the present application, it was found that, by combining in the lipid phase constituting the membrane of the vesicles certain polyol esters with at least one ionic lipid selected from a certain group, vesicles stable to hydrolysis were obtained.

The subject of the present invention is, consequently, a composition composed of an aqueous dispersion of vesicles consisting of a membrane of lipid phase encapsulating an aqueous phase, the lipid phase comprising nonionic amphiphilic lipids and at least one ionic amphiphilic lipid, characterized in that:

the nonionic amphiphilic lipids consist of a mixture of esters of at least one polyol chosen from the group composed of polyethylene glycol containing from 1 to 60 ethylene oxide units, sorbitan, sorbitan bearing 2 to 60 ethylene oxide units, glycerol bearing 2 to 30 ethylene oxide units, polyglycerols containing 2 to 15 glycerol units, sucroses, and glucoses bearing 2 to 30 ethylene oxide units and of at least one fatty acid containing a saturated or unsaturated, linear or branched $C_5$–$C_{17}$ alkyl chain, the number of alkyl chains per polyol group being between 1 and 10; and in that the ionic amphiphilic lipid or lipids is/are chosen from the group composed of those which impart a pH of between 5.5 and 7.5 to the dispersion;

the weight ratio of the quantity of nonionic amphiphilic lipids to that of ionic amphiphilic lipid or lipids in the lipid phase being between 50:1 and 50:25 and the weight ratio of the lipid phase to the aqueous dispersion phase being between 1:1,000 and 300:1,000.

It was found that, in the composition according to the invention, the vesicles obtained were stable in water, in the absence of buffered saline solutions, after storage for 2 months at temperatures between room temperature and 45° C.; they consequently have sufficient stability to be able to be used in cosmetic and dermopharmaceutical compositions.

The composition according to the invention hence makes it possible to benefit from the advantage of polyol esters, which is that of being degradable under the action of the pH of the skin or by the enzymes of the skin. Their degradation gives rise to products which, in most cases, have a cosmetic or dermopharmaceutical action on the skin. In effect, free fatty acids such as palmitic acid or stearic acid have a bacteriostatic activity, and polyols such as glycerol, polyglycerols, sorbitol or sucrose are humectants and can, where appropriate, provide a supply of energy.

The vesicles obtained afford a good degree of encapsulation of water-soluble substances and low permeability. They hence permit the encapsulation of water-soluble active agents. Furthermore, the gradual degradation of the vesicles on the skin permits a controlled release of the water-soluble active agents possibly contained in the encapsulated aqueous phase or the fat-soluble active agents possibly contained in the lipid phase.

The dispersions of the vesicles of the composition according to the invention may be prepared by any known process for the manufacture of vesicles of amphiphilic lipids, and more especially by the so-called "lipid co-melting" process, enabling them to be prepared simply on an industrial scale.

In the present application and the claims, the expression "mixture of esters" not only covers mixtures of pure esters of different chemical families, but also covers any product which contains several chemically pure polyol esters of the same family in variable proportions. This applies especially to products having a statistical formula in their hydrophilic portion, for example a polyglycerol ester of formula $$RCO + OCH_2 - CHOH - CH_2 +_{\overline{n}} OH$$

where $\overline{n}$ is a statistical value and which can contain various proportions of esters for which n=1, n=2, n=3, n=4, etc; this also applies to esters containing several alkyl chains in their lipophilic portion, such as cocoates, which contain from $C_5$ to $C_{17}$ alkyl chains, or isostearates, where the $C_{17}$ alkyl chains are a complex mixture of isomeric forms; it likewise applies to products consisting of mixtures of mono-, di-, tri- or polyesters of the same polyol. It should be noted that a product which contained only a single ester capable of forming vesicles and impurities of some other type could not be used according to the invention.

Commercial esters which are usable alone according to the invention, since they are in actual fact mixtures of esters, are, for example, the following:

the partial esters of sorbitan (or sorbitol anhydride) and of fatty acid sold by the company "ICI" under the trade names Span 20, 40, 60 and 80®;

the sorbitan isostearate sold by the company "Nikko" under the trade name SI 10 R NIKKOL®;

the sorbitan stearate bearing 4 ethylene oxide units sold by the company ICI under the name TWEEN 61®;

the polyethylene glycol stearate containing 8 ethylene oxide units sold by the company ICI under the name MYRJ 45®;

the polyethylene glycol monostearate of formula $$OHCH_2(CH_2OCH_2)_n - CH_2OH$$

in which formula $\overline{n}$ is equal to 4, sold by the company Nikko under the name MYS 4®;

the polyethylene glycol stearate of molecular weight 400, chemical grade or grade produced by biotechnology, sold by the company Unichema;

the diglyceryl stearate bearing 4 ethylene oxide units sold by the company Hoechst under the name HOSTACERINE DGS®;

the tetraglycerol stearate sold by the company Nikko under the name TETRAGLYN 1S®;

the diglyceryl isostearate sold by the company Solvay;

the diglyceryl stearate sold by the company Nihon under the name EMALEX DSG 2®;

the sucrose mono-, di- and tripalmitostearates sold by the company Croda under the names F50, F70, F110 and F160 CRODESTA®;

the mixture of sucrose mono- and dipalmitostearates sold by the company Grillo under the name Grilloten PSE 141 G®;

the mixture of sucrose stearate and sucrose cocoate sold by the company ICI under the name Arlatone 2121®;

the methylglucose distearate bearing 20 ethylene oxide units sold by the company Amerchol under the name GLUCAM E 20 DISTEARATE®.

Mixtures with one another of these different products, which are already mixtures, or mixtures of these products with pure products may naturally be used.

The ionic amphiphilic lipid or lipids combined with the nonionic amphiphilic lipids according to the invention is/are preferably selected from the group composed of:

(1) neutralized anionic lipids, these anionic lipids preferably being chosen from:

the alkali metal salts of dicetyl phosphate and of dimyristyl phosphate, especially the Na and K salts;

the alkali metal salts of cholesterol sulphate, especially the Na salt;

the alkali metal salts of cholesterol phosphate, especially the Na salt;

mono- and disodium acylglutamates;

phosphatidic acid sodium salt;

(2) amphoteric lipids, these amphoteric lipids preferably being phospholipids, especially pure soya bean phosphatidylethanolamine;

(3) alkylsulphonic derivatives, these derivatives preferably being the compounds of the formula:

$$\begin{array}{c} O \\ \parallel \\ R \diagdown \diagup C - O + CH_2CH_2O \overline{)_{\frac{1}{2}}} CH_3 \\ C \\ \diagup \diagdown \\ H \quad SO_3M \end{array}$$

in which formula R represents $C_{16}H_{33}$ and $C_{18}H_{37}$ radicals taken mixed or separately and M is an alkali metal, preferably sodium.

It is possible, in a known manner, to incorporate in the lipid phase constituting the lipid membrane of the vesicles at least one additive whose main function is to decrease the permeability of the vesicles, to prevent their flocculation and their fusion and to increase the degree of encapsulation.

According to the invention, it is possible to add to the lipid phase at least one additive preferably chosen from the group composed of:

sterols, and in particular phytosterols and cholesterol, long-chain alcohols and diols, long-chain amines and their quaternary ammonium derivatives.

These additives can optionally have cosmetic and/or dermopharmaceutical activity. This applies, for example, to cholesterol.

The vesicles of the compositions according to the invention can contain, in a known manner, one or more active compound(s) having cosmetic and/or dermopharmaceutical activity, which, depending on their solubility properties, can have different locations. If the active agents are water-soluble, they are introduced into the encaspulated aqueous phase of the vesicles. If the active agents are fat-soluble, they are introduced into the lipid phase constituting the membrane. If the active agents are amphiphilic, they distribute between the lipid phase and the encapsulated aqueous phase, with a partition coefficient which varies according to the nature of the amphiphilic active agent and the respective compositions of the lipid phase and of the encapsulated aqueous phase.

The water-soluble active agents are, for example, glycerol, sorbitol, erythrulose and antibiotics. The fat-soluble or partially fat-soluble (amphiphilic) active agents are chosen from those which do not significantly increase the permeability of the vesicles, do not cause their flocculation and their fusion and do not decrease the degree of encapsulation. It is advantageous to use fat-soluble active agents which also constitute additives.

Preferred fat-soluble active agents according to the invention are chosen from the group composed of:

sphingomyelins, glycoceramides, especially those obtained from wheat germ and natural or synthetic ceramides, preferably those described in French Patent Application No. 91/02,091 filed on 21st Feb. 1991, which are of the formula:

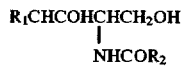

(I)

in which formula:

$R_1$ represents a $C_{11}-C_{21}$ alkyl or alkenyl radical, $R_2$ represents:

a saturated $C_{11}-C_{23}$ hydrocarbon radical, a mixture of saturated, linear $C_{11}-C_{19}$ hydrocarbon radicals bearing at least one ethylenic unsaturation, and preferably one or two, in which mixture the proportion of saturated radicals cannot exceed 35%, the ceramide of formula (I) being in the form of a racemic mixture of erythro and threo diastereoisomers in erythro/threo proportions of between 85:15 and 60:40.

According to the invention, it is preferable to introduce into the lipid phase constituting the membrane a mixture of ceramide(s) and cholesterol. In effect, the use of this mixture is especially advantageous, since it enables the lipids of the skin to be reconstituted when the vesicles of the dispersion according to the invention degrade on the skin.

The active agents introduced, be they hydrophilic, lipophilic or amphiphilic, can have highly variable cosmetic and/or dermopharmaceutical activities (or "functions"), which are given in Table I below:

TABLE I

| FUNCTION | ACTIVE AGENTS WHICH ARE USABLE |
| --- | --- |
| Antioxidant or anti-free-radical | Extracts of the following plants: Hawthorn. Ginkgo biloba. Green tea. Vine. Rosemary. Enzymes: Marketed by Sederma under the name SB 12 ®, and consisting of a mixture of lactoferrin and lactoperoxidase, glucose oxidase and potassium thiocyanate. Superoxide dismutase. Glutathione peroxidase. Superphycodismutase extracted from algae. COENZYMES Q, especially coenzyme Q10 ®. Sequestering agents, especially polyphosphonic acid derivatives. Tannins. Selenium and its derivatives, especially seleno methionine. Peptides, for example a mixture of spleen and thymus extracts. Thiolim and unstabilized bovine serum albumin. Proteins, for example haemocyanin, which is a copper-containing protein extracted from marine snails, and apohaemocyanin, which is a similar protein without copper. Flavonoids, in particular catechin, proanthocyanidins, flavanols, flavones, isoflavones, flavanenols, flavanones, flavans and chalcones. Carotenoids, in particular β-carotene and annatto. Sorbohydroxyamic acid. Tocopherols, in particular alpha-tocopherol and alpha-tocopherol acetate. Ascorbyl palmitate. Propyl gallate. Caffeic acid and its derivatives. Ascorbic acid. Homogentisic acid. Erythorbic acid. Nordihydroguaiacetic acid. Lysine laurylmethionate. Butylated hydroxyanisole. Butylated hydroxytoluene. "SOD-like" substances. |
| Hydrating or humectant | A reconstitution of sweat ("Normal moisturizing factors" - NMF). Sodium pyroglutamate. Hyaluronic acid. Chitosan derivatives (carboxymethylchitin). β-Glycerophosphate. Lactamide. Acetamide Ethyl, sodium and triethanolamine lactates. Metal pyrrolidonecarboxylates, especially those of Mg, Zn, Fe, Ca or Na. Thiamorpholinone. Orotic acid. alpha-hydroxylated $C_3$ to $C_{20}$ carboxylic acids, in particuiar alpha-hydroxypropionic acid. Polyols, in particular inositol, glycerol, diglycerol, sorbitol. Polyol glycosides, in particular alginate and guar. Proteins, in particular gelatin and soluble collagen. Lipoprotideus chosen from mono- or polyacylated derivatives of amino acids or of polypeptides in which the acid residue RCO contains a $C_{13}-C_{19}$ hydrocarbon chain, in particular palmitoylcaseinic acid, palmitoylcollagenic acid, the O,N-dipalmitoyl derivative of hydroxyproline, sodium stearoylglutamate, collagen stearoyl tripeptide, collagen oleyl tetra- and pentapeptide, hydroxyproline linoleate. Urea and its derivatives, in particular methylurea. Skin tissue extract, in particular that marketed by Laboratoires Serobiologiques de Nancy (LSN) under |

TABLE I-continued

| FUNCTION | ACTIVE AGENTS WHICH ARE USABLE |
| --- | --- |
| | the name OSMODYN ® and containing peptides, amino acids, saccharides and 17% of mannitol. More especially, a combinatian of glycerol, urea and palmitoylcaseinic acid. |
| Melanoregulator: 1) suntan accelerator 2) Depigmenting | Bergamot and citrus oils. alpha-MSH and its synthetic homologues. Caffeine. Tyrosine derivatives, in particular glucose tyrosinate and N-malyltyrosine. Ascorbic acid or vitamin C and its derivatives, in particular Mg ascorbyl phosphate. Hydroxy acids, in particular glycolic acid. Kojic acid. Arbutin and its derivatives. Haemocyanin (copper-containing protein of the marine snail) and apohaemocyanin (protein similar to the above without copper). Hydroquinone and its derivatives, in particular the monoalkyl ether and the benzyl ether |
| Skin coloration (artificial suntan) | ortho-Diacetylbenzene. Indoles. Dihydroxyacetone. Erythrulose. Glyceraldehyde. gamma-Dialdehydes, in particular tartraldehyde. |
| Liporegulators (slimming and anti-acne, anti-seborrhoea) | Complexes of vitamins and trace elements, in particular the vitamin $B_6$/zinc complex. Orizanol. Azelaic acid. Xanthines and alkylxanthines, in particular extract of cola, caffeine and theophilline. Cyclic and acyclic adenosine monophosphate. Adenosine triphosphate. Ivy extract. Horse chestnut extract. Extracts of algae, in particular extract of red algae (Fucus serratus) and cytofiltrate. Ginseng extract. Centella asiatica extract (asiaticoside) containing genin and asiatic acid. Thioxolone (HBT). S-Carboxymethylcysteine. S-Benzylcysteamine. |
| Anti-ageing and anti-wrinkle | Unsaponifiables, for example of soya bean and avocado. Unsaturated fatty acids, in particular linoleic acid and linolenic acid. Hydroxy acids, in particular glycolic acid. Growth factors. Trace element/vitamin use complexes, in particular $B_6$/Zn. 5-n-Octanoylsalicylic acid. Adenosine. Retinol and its derivatives, in particular retinol acetate and retinol palmitate. Retinoids, in particular cis- or trans-retinoic acids and those described in Patents FR-A-2,570,377; EP-A-199,636; and EP-A-325,540 and European Patent Application 90-402072. Combination of retinoids and xanthines. Hydroxyproline. Sialic acids. The unstabilized extract of spleen, of thymus, Thiolim and bovine serum albumin sold by the company Silab under the trade name SILAB ®. An animal placental extract, in particular 5.5% bovine placental embryonic extract in water, stabilized with 0.2% of exyl K100a (matrix). Proteoglycans, especially stabilized 5% bovine tracheal cartilage proteoglycan (proteodermin). Colostrum. Cell oxygenation factors, in particular octacosamol. |
| Anti-UV | UV screening agents, in particular 2-ethylhexyl para-methoxycinnamate; benzophenone, benzylidenecamphor and their derivatives, especially 2,2',4,4'-tetrahydroxybenzophenone and 2 hydroxy-4-methoxybenzophenone-5-sulphonic acid; para-aminobenzoic acid, dipropylene glycol salicylate, octyl salicylate, the dibenzoylmethane derivatives sold under the brand names EUSOLEX 8020 ® × PARSOL 1789 ® and the product's sold under the brand names EUSOLEX 232 ® , UNIVUL T 150 ® , UNIVUL N 539 ® , Escalol 507 ® . |
| Keratolytic | Salicylic acid and its derivatives such as alkylsalicylic acids, in particular, 5-n-octanoyl- and 5-n-dodecanoylsalicylic acids, N-hexadecylpyridinium salicylate. Retinoic acid. Proteolytic enzymes, in particular trypsin, alpha-chymotrypsin, papain, bromelain and pepsin. Benzoyl peroxide. Urea. alpha-Hydroxy acids. |
| Emollient Anti-inflammatory | Esters such as isopropyl adipate. Corticoids such as β-methasone 17-acetate, indomethacin, ketoprofen, flufenamic acid, ibuprofen, dichlofenac, diflunisal, fenclofenac, naproxen, piroxidam and sulindac Glycerol monostearyl ether (batyl alcohol) and glycerol monocetyl ether (chimyl alcohol). Glycyrrhetinic acid and its salts, in particular the ammonium salt. alpha-Bisabolol (chamomile extract). Shikonin. Extracts of plants such as arnica, aloe, cornflower water. Extracts of meristematic tissue, in particular oak root extract. Plankton. |
| Cooling | Menthol. Menthyl lactate. |
| Cicatrizing | Mimosa tenui flora extract. Centella asiatica extract. β-Glycyrrhetinic acid. Hydroxyproline. Arginine. A placental extract. A yeast extract. Fagaramide. H-Acetylhydroxyproline. Acexamic acid and its derivatives. |
| Vasoprotective | Flavonoid, in particular rutin derivatives such as etoxazorutin and sodium rutin propylsulphonate. Plant extracts, in particular Ginkgo biloba oily extract and extract of horse cheatnut (escin), of ivy (saponins) and of butcher's broom. alpha-Tocopherol nicotinate. |
| Anti-bacterial, antifungal | Trimethylcetylammonium bromide. Sorbic acid. Benzoyl peroxide. Cetylpyridinium chloride. Benzalkonium chloride. para-Hydroxybenzoic acid and its salts. 2-Bromo-2-nitro-1,3-propanediol. 3,4,4'-Trichlorocarbanilide. 2,4,4'-Trichloro-2-hydroxydiphenyl ether. Dehydroacetic acid. A grapefruit extract in glycerol and propylene glycol. Chlorhexidine. Hexetidine Hexamidine. |
| Insect-repellent agent | Dimethyltoluamide. |
| Antiper- | Aluminum chlorohydrate. |

TABLE I-continued

| FUNCTION | ACTIVE AGENTS WHICH ARE USABLE |
|---|---|
| spirant | Aluminum chloride. |
| | Sodium lactate/aluminum chlorohydroxy complex. |
| | Zirconyl chlorohydrate. |
| Deodorant | Zinc oxide. |
| | Zinc ricinoleate. |
| | 2-Ethyl-1,3-hexanediol. |
| | Hexachlorophene. |
| | The product sold under the brand name IRGASAN DP 300 ®. |
| Antidand-ruff | Octopyrox. |
| | Omadines. |
| | Coal tar. |
| | 1-Hydroxy-4-methyl-2,4,4-trimethyl-6-pentyl-2-pyridinone |
| | Selenium sulphide. |
| Anti-hair loss | Glucuronidonase inhibitors. |
| | Muccopolysaccharides |
| | Methyl or hexyl nicotinate. |
| | Forskolin. |
| | Monoxidil. |
| | Xanthines. |
| | Retinoids. |
| Hair colorant | Oxidation bases and couplers. |
| | Direct dyes. |
| | Self-oxidizing dyes. |
| Hair bleaching agent | Hydrogen peroxide. |
| Reducing agent for permanent-waving | Thioglycolic acid. |
| | Cysteine. |
| | Cysteamine. |
| | N-Acetylcysteine. |
| | N-Acetylcysteamine. |
| | Glycerol thioglycolate. |
| skin and hair conditioner | Cationic polymers, cations. |

The different active agents used can all be fat-soluble, water-soluble or amphiphilic, or can belong to at least two of these categories. The active agents introduced can have the same function or different functions. It should be noted that some active agents have several functions.

The aqueous phase of the dispersion of the composition according to the invention can also contain a dispersion of droplets of a water-immiscible liquid, as described in French Patents 2,485,921 and 2,490,504. It has, in effect, been found that the vesicles according to the invention stabilize the dispersion of droplets of water-immiscible liquid without it being necessary to introduce a conventional emulsifier.

The water-immiscible liquid, which can be present in the form of a dispersion in the aqueous dispersion phase, can, in particular, be chosen from the group composed of:

animal or vegetable oils composed of esters of a fatty acid and of polyols, especially liquid triglycerides, for example sunflower, maize, soya bean, gourd, grape-pip, jojoba, sesame and hazelnut oils, fish oils, glycerol tricaprocaprylate, or vegetable or animal oils of formula $R_9COOR_{10}$, in which formula $R_9$ represents the residue of a higher fatty acid containing from 7 to 19 carbon atoms and $R_{10}$ represents a branched hydrocarbon chain containing from 3 to 20 carbon atoms, for example Purcellin oil;

natural or synthetic essential oils such as, for example, eucalyptus, lavandin, lavender, vetiver, Litsea cubeba, lemon, sandal wood, rosemary, chamomile, savory, nutmeg, cinnamon, hyssop, caraway, orange, geraniol, cade and bergamot oils;

hydrocarbons such as hexadecane and liquid petrolatum;

halocarbons, in particular fluorocarbons such as fluoroamines, for example perfluorotributylamine, fluorinated hydrocarbons, for example perfluorodecahydronaphthalene, fluoro esters and fluoro ethers;

silicones, for example polysiloxanes, polydimethylsiloxanes and fluorosilicones;

esters of an inorganic acid and of an alcohol; and ethers and polyethers.

The aqueous dispersion phase can also contain water-soluble cosmetic and/or dermopharmaceutical active agents. The water-immiscible liquid can optionally contain a fat-soluble active agent.

The aqueous dispersion phase can also contain adjuvants having neither cosmetic activity nor dermopharmaceutical activity of their own, but which are used for the formulation of the dispersion in the form of a lotion, cream or serum. These adjuvants are, in particular, selected from the group composed of gelling agents, preservatives, colorants, pigments, fillers, opacifiers and perfumes.

Among gelling agents which are usable, there may be mentioned cellulose derivatives such as hydroxyethylcellulose, derivatives of algae such as satiagum, natural gums such as tragacanth, and synthetic polymers, especially the mixtures of polyvinylcarboxylic acids marketed by the company Goodrich under the name Carbopol and the mixture of Na acrylate/acrylamide copolymers marketed by the company Hoechst under the name Hostacherin PN 73®.

Among pigments which are usable according to the invention, special mention may be made of pigments coated with silicones, with fluorinated compounds such as perfluoroalkyl phosphates or polytetrafluoroethylene (sold under the trade name Tefon®) or with amino acids; these coated pigments can be, in particular, oxides of iron or of titanium. As an example, there may be mentioned products sold by the company Wackherr under the trade name COVAFLUOR®, which are, in particular, oxides of iron or of titanium coated with perfluoroalkyl phosphate; there may also be mentioned the products sold by the company Clark Color under the trade name TEFLON TREATED PIGMENTS®, which are, in particular, oxides of iron or of titanium coated with polytetrafluoroethylene.

Among fillers which are usable according to the invention, special mention may be made of talc, mica, starch powder, nylon powder and silica powder.

In the composition according to the invention, the vesicles generally have an average diameter of between 10 and 5,000 nm. When the aqueous phase contains a dispersion of droplets of water-immiscible liquid, these droplets advantageously have an average diameter of between 100 and 10,000 nm.

The examples below, given purely by way of illustration and without implied limitation, enable a better understanding of the invention to be gained.

In all the examples given below, the dispersions of vesicles are prepared by the so-called "lipid co-melting" process, in which:

in a first phase, the lipid phase is prepared by mixing in liquid form the different amphiphilic lipids of which it is composed, where appropriate combined with fat-soluble active agents or additives, and the lipid phase obtained is brought into contact with an aqueous phase containing, where appropriate, water-soluble active agents, so as to obtain a lamellar phase, in a second phase, an aqueous dispersion phase containing, where appropriate, a water-immiscible liquid and different additives is added to the hydrated lamellar phase obtained, and in a third phase, the mixture is subjected to vigorous agitation in a homogenizer to obtain vesicles dispersed in an aqueous dispersion phase.

EXAMPLE 1

By way of comparison, vesicles were prepared from a lipid phase containing, as a nonionic lipid, one or other of the following two products A and B:

A) Sorbitan palmitate marketed by the company ICI under the name SPAN 40®, which is a mixture containing predominantly sorbitan monopalmitate and small quantities of sorbitan di-, tri- and tetrapalmitate;

B) The chemically pure compound of formula:

$$C_{15}H_{31}CO(OCH_2CHOHCH_2)_2OH$$

When the product A is used, the composition obtained as described below is within the scope of the invention, whereas this is not the case with the product B.

The composition has the following formulation:

| | |
|---|---|
| Nonionic lipid A or B | 1.425 g |
| Cholesterol | 1.425 g |
| Monosodium glutamate marketed by the company Ajinomoto under the name ACYLGLUTAMATE HS 11 ® | 0.15 g |
| Preservative | 0.02 g |
| Water qs | 100 g |

A dispersion containing vesicles 250 nm in-size was obtained after homogenization.

The two dispersions obtained were subjected to a stability test by subjecting them to 5 successive cycles of temperature variation between −20° C. and +20° C., each cycle proceeding in the following manner:

10 hours at −20° C.

2 hours from −20° to +20° C.

10 hours at +20° C.

The temperature changes take place with a gradient of 0.33° C./min.

At the end of the cycles, the dispersion of vesicles containing the nonionic lipid A according to the invention and that of vesicles containing the chemically pure nonionic lipid B (composition not forming part of the invention) were observed by eye and using an optical microscope. It was found that the vesicles containing the nonionic lipid A according to the invention are intact, while the vesicles containing the nonionic lipid B are massively recrystallized.

EXAMPLES 2 to 6

By way of comparison, compositions containing a dispersion of vesicles in which the lipid phase contains an ionic lipid forming part of the invention, and compositions containing a dispersion in which the livid phase contains an ionic lipid not forming part of the invention, were prepared.

The formulation of the lipid phases used in the different examples is given in Table II below:

TABLE II

| | Examples | | | | |
|---|---|---|---|---|---|
| | 2 | 3 | 4 | 5 | 6 |
| Tetraglycerol stearate marketed by the company Nikko | 47.5 | — | 47.5 | — | — |
| Diglyceryl isostearyl marketed by the company Solvay | — | 90 | — | 90 | — |
| Sorbitan palmitate markted by the company ICI under the name SPAN 40 ® | — | — | — | — | 45 |
| Cholesterol | 47.5 | — | 47.5 | — | 45 |
| Dicetyl acid phosphate | 5 | 10 | | | |
| Glutamate marketed by the company Ajinomoto under the name ACYLGLUTAMATE HS 11 ® | | | 5 | 10 | 10 |
| pH of the aqueoua diaperaion (1) | 3.3 | 3.2 | 6.3 | 6.3 | 6.1 |

(1) The pH was measured on dispersions containing 2% of lipid and 0.1% of preservative.

The diameter of the vesicles at time T0 immediately after their formation and after 2 months of storage at room temperature (RT), at 37° C. and at 45° C. were measured using an AMTECH BI 90 ® laser granulometer; the results are given in Table III below:

TABLE III

| AVERAGE DIAMETER OF THE VESICLES IN MICRONS | | | | |
|---|---|---|---|---|
| Lipid combination tested | at time T0 | after 2 months | | |
| | | at RT | at 37° C. | at 45° C. |
| Example 2 | 0.24 | S | C | C++ |
| Example 3 | 0.09 | S | S | 0.18-U |
| Example 4 | 0.25 | S | S | S |
| Example 5 | 0.19 | S | S | S |
| Example 6 | 0.24 | S | S | S |

S: vesicles of stable diameter
U: vesicles of unstable diameter
C: presence of crystals
C++: massive presence of crystals This Table III shows that the presence of an acidic anionic lipid not forming part of the invention (Examples 2 and 3) does not enable the vesicles to be stabilized, while a neutralized anionic lipid according to the invention (Examples 4 to 6) enables the vesicles to be stabilized.

EXAMPLE 7

Biodegradability of the vesicles according to the invention under the effect of the enzymes of superficial layers of human skin.

A vesicular composition having the following formulation (% by weight) was prepared:

| | |
|---|---|
| Sorbitan palmitate sold by the company ICI under the name SPAN 40 ® | 1.425% |
| Cholesterol | 1.425% |
| Monosodium glutamate marketed by the company Ajinomoto under the name ACYLGLUTAMATE HS 11 ® | 0.15% |

| | |
|---|---|
| Glycerol | 3.00% |
| Preservative NaN$_3$ | 0.02% |
| Water qs | 100% |

The pH of the aqueous dispersion phase is 6.0 and the diameter of the vesicles is 260 nm.

In addition, an enzymatic liquor was prepared by treatment of an area of the skin of the back measuring 4×4 cm which has undergone 8 successive strips. The enzymatic material is extracted with acetone and then liophilized. The powder obtained is dissolved in 0.5 ml of the above dispersion of vesicles.

The palmitic acid released into the reaction mixture after 0 to 7 days of incubation at 37° C. is assayed. The assay of palmitic acid released is performed by two processes:

1) by high performance thin-layer chromatography under the following conditions:
   Eluent: Hexane/petroleum ether/acetic acid 80:20:3 (by volume)
   Visualizing agent: 4% (by weight) copper sulphate in 15% (by weight) orthophosphoric acid
   Treatment: Carbonization at 180° C. for 5 minutes
   Reading: Shimadzu densitometer at 540 nm.
2) using Bohringer enzyme kit No. 10 82 914 for assay of free fatty acids calibrated on palmitic acid.

The two assays give concordant results.

In Table IV below, the quantity of palmitic acid released is given in % relative to the total present at the start in the form of sorbitan palmirate.

TABLE IV

| Incubation time | Palmitic acid |
|---|---|
| 15 hours | 3% |
| 3 days | 23% |
| 7 days | 40% |

The vesicles according to the invention hence permit a delayed release of the active agents present in the vesicles, either in the encapsulated aqueous phase, or in the lipid membrane.

EXAMPLE 8

Day cream for the face intended for the care of dry skins.

The cream is prepared by the process defined above.

In a first phase, the formulation used for the vesicular composition is as follows:

| | |
|---|---|
| Sorbitan palmitate marketed by the company ICI under the name SPAN 40 ® | 3.8 g |
| Cholesterol | 3.8 g |
| N-Stearoylglutamic acid monosodium salt marketed by the company Ajinomoto under the name ACYLGLUTAMATE HS 11 ® | 0.4 g |
| Demineralized water qs | 50 g |
| Preservatives | 0.3 g |
| Glycerol | 5.0 g |

In a second phase, the formulation of the dispersion of oil is as follows:

| | |
|---|---|
| Macadamia oil | 16.0 g |
| Perfume | 0.2 g |
| Mixture of polyvinylcarboxylic acids marketed by the company Goodrich under the name CARBOPOL 940 ® | 0.42 g |
| | 0.42 g |
| Triethanolamine qs | pH 6 |
| Demineralized water qs | 100 g |

In a third phase, the two formulations are mixed as described above to obtain the composition according to the invention.

After a week of daily application every morning to the carefully cleansed face, an improvement is seen in the appearance and radiance of skin of the face, which becomes smoother, firmer and more hydrated with a more radiant complexion.

EXAMPLE 9

Anti-ageing day cream for the face.

A cream having the following formulation is prepared as in Example 8:

| First phase: | |
|---|---|
| Sorbitan stearate marketed by the company ICI under the name SPAN 60 ® | 3.8 g |
| Cholesterol | 3.8 g |
| N-Stearoylglutamic acid monosodium salt marketed by the company Ajinomoto under the name ACYLGLUTAMATE HS 11 ® | 0.4 g |
| Glycerol | 3.0 g |
| L-Hydroxyproline | 1.0 g |
| D-Panthenol | 1.5 g |
| Guanosine | 0.01 g |
| Demineralized water qs | 50 g |
| Preservatives | 0.3 g |
| Polyphosphonate marketed by the company Monsanto Chemical under the name DEQUEST 2046 ® | 0.8 g |
| Lactic hydrolysate marketed by "Laboratoires Serobiologiques de Nancy" under the name LACTOLAN LS ® | 5.0 g |
| L-Serine | 0.2 g |
| Second phase: | |
| Propyl para-hydroxybenzoate | 0.3 g |
| Macadamia oil | 7.0 g |
| Natural concentrates of tocopherols | 4.0 g |
| Sunscreen agents | 1.0 g |
| Volatile silicone oil | 7.5 g |
| Vitamin F glycerides | 3.0 g |
| Mixture of polyvinylcarboxylic acids marketed by the company Goodrich under the name CARBOPOL 940 ® | 0.5 g |
| Methyl para-hydroxybenzoate | 0.2 g |
| Triethanolamine qs | pH 6.5 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 10

Anti-ageing serum for the face.

A serum having the following formulation is prepared:

| | |
|---|---|
| Sorbitan laurate marketed by the company ICI under the name SPAN 20 ® | 1.5 g |
| Cholesterol | 0.4 g |
| N-Stearoylglutamic acid monosodium salt marketed by the company Ajinomoto under the name ACYLGLUTAMATE HS 11 ® | 0.1 g |
| Glycerol | 3.0 g |
| L-Hydroxyproline | 1.0 g |
| D-Panthenol | 1.5 g |
| Guanosine | 0.01 g |
| Preservatives | 0.3 g |
| Polyphosphonate marketed by the company Monsanto Chemical under the name DEQUEST 2046 ® | 0.8 g |
| Lactic hydrolysate marketed by "Laboratoires Serobiologiques de Nancy" under the name LACTOLAN LS ® | 5.0 g |
| L-Serine | 0.2 g |
| Aqueous solution of superoxide dismutase containing 5,000 units per ml, marketed by the company Pentapharm | 1.0 g |
| Mixture of polyvinylcarboxylic acids marketed by the company Goodrich under the name CARBOPOL 940 ® | 0.3 g |
| L-Lysine monohydrate qs | pH 6.5 |
| Demineralized water qs | 100 g |

After application twice a day for three weeks, a marked firming of the skin is noted.

EXAMPLE 11

Anti-ageing serum for the face.

A serum having the following formulation is prepared:

| | |
|---|---|
| Sorbitan oleate marketed by the company ICI under the name SPAN 80 ® | 0.75 g |
| Cholesterol | 0.20 g |
| Phosphatidic acid sodium salt | 0.05 g |
| Glycerol | 3.0 g |
| L-Hydroxyproline | 1.0 g |
| D-Panthenol | 1.5 g |
| Preservatives | 0.3 g |
| Guanosine | 0.01 g |
| Polyphosphonate marketed by the company Monsanto Chemical under the name DEQUEST 2046 ® | 0.8 g |
| Lactic hydrolysate marketed by "Laboratoires Serobiologiques de Nancy" under the name LACTOLAN LS ® | 5.0 g |
| L-Serine | 0.2 g |
| Aqueous solution of superoxide dismutase containing 5,000 units per ml, marketed by the company Pentapharm | 1.0 g |
| Mixture of polyvinylcarboxylic acids marketed by the company Goodrich under the name CARBOPOL 940 ® | 0.3 g |
| L-Lysine monohydrate qs | pH 6.5 |
| Demineralized water qs | 100 g |

It was observed that the vesicles contained in the serum remained stable after 3 months of storage. After application twice a day for 3 weeks, a marked firming of the skin is noted.

EXAMPLE 12

Day cream for the face.

A cream having the following formulation was prepared:

| | |
|---|---|
| First phase: | |
| 4-mol oxyethylenated sorbitan stearated marketed by the company ICI under the name TWEEN 61 ® | 3.8 g |
| Cholesterol | 3.8 g |
| N-Stearoylglutamic acid monosodium salt marketed by the company Ajinomoto under the name ACYLGLUTAMATE HS 11 ® | 0.4 g |
| Glycerol | 5.0 g |
| Preservatives | 0.3 g |
| Demineralized water qs | 50 g |
| Second phase: | |
| Macadamia oil | 16.0 g |
| Perfume | 0.2 g |
| Mixture of polyvinylcarboxylic acids marketed by the company Goodrich under the name CARBOPOL 940 ® | 0.42 g |
| Triethanolamine qs | pH 6 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 13

Day cream for the face.

A cream having the following formulation was prepared:

| | |
|---|---|
| First phase: | |
| 8-mol oxyethylenated sorbitan stearate marketed by the company ICI under the name MYRJ 45 ® | 4.4 g |
| Cholesterol | 3.2 g |
| N-Stearoylglutamic acid disodium salt marketed by the Ajinomoto under the name ACYLGLUTAMATE HS 21 ® | 0.4 g |
| Glycerol | 5.0 g |
| Prservatives | 0.3 g |
| Demineralized water qs | 50 g |
| Second phase: | |
| Macadamia oil | 16.0 g |
| Perfume | 0.2 g |
| Mixture of polyvinylcarboxylic acids marketed by the company Goodrich under the name CARBOPOL 940 ® | 0.42 g |
| Triethanolamine qs | pH 6 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 14

Day cream for the face.
A cream having the following formulation is prepared:

| First phase: | |
|---|---|
| Tetraglycerol stearate marketed by the company Nikko under the name TETRAGLYN 1S ® | 3.8 g |
| Cholesterol | 3.8 g |
| N-Stearoylglutamic acid monosodium salt marketed by the company Ajinomoto under the name ACYLGLUTAMATE HS 11 ® | 0.4 g |
| Glycerol | 5.0 g |
| Preservatives | 0.3 g |
| Demineralized water qs | 50 g |
| Second phase: | |
| Macadamia oil | 16.0 g |
| Perfume | 0.2 g |
| Mixture of polyvinylcarboxylic acids marketed by the company Goodrich under the name CARBOPOL 940 ® | 0.42 g |
| Triethanolamine qs | pH 6 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 15

Day cream for the face.
A cream having the following formulation is prepared:

| First phase: | |
|---|---|
| Sorbitan palmitate marketed by the company ICI under the name SPAN 40 ® | 1.0 g |
| Synthectic ceramide corresponding to the formula | 1.0 g |
| $R_1CHOHCHCH_2OH$        (I)<br>     |<br>     $NHCOR_2$ | |
| for which $R_1$ and $R_2$ and $C_{15}H_{31}$, and which is a mixture of the erythro and thero forms in the proportion 70:30 | |
| Cholesterol | 0.7 g |
| Cholesterol sulphate sodium salt | 0.30 g |
| Glycerol | 3.0 g |
| Preservatives | 0.3 g |
| Oxyethylenated sorbitan laurate containing 20 mol of EO, marketed by the company ICI under the name TWEEN 20 ® | 1.0 g |
| Demineralized water qs | 50 g |
| Second phase: | |
| Volatile silicone oil | 10.0 g |
| Apricot-kernel oil | 10.0 g |
| Perfume | 0.2 g |
| Mixture of polyvinylcarboxylic acids marketed by the company Goodrich under the name CARBOPOL 940 ® | 0.42 g |
| Triethanolamine qs | pH 6.5 |
| Demineralized water qs | 100 g |

After decomposition of the sorbitan palmirate and sorbitan laurate by the enzymes of the skin, this cream makes it possible to treat the skin with palmitic acid, lauric acid, sorbitol, a ceramide and cholesterol, and provides the skin with especially effective protection. Applied daily for 20 days to a tired skin, this cream gives noticeable results.

EXAMPLE 16

Anti-ageing serum.
A serum having the following formulation is prepared:

| Sorbitan palmitate marketed by the company ICI under the name SPAN 40 ® | 0.17 g |
|---|---|
| Synthetic ceramide corresponding to the formula | 0.17 g |
| $R_1CHOHCHCH_2OH$        (I)<br>     |<br>     $NHCOR_2$ | |
| for which $R_1$ is $C_{15}H_{31}$ and R2 is the residue of oleyl chloride, marketed by the company BASF with an acid chloride titre of 98% and which is a mixture of the erythro and threo forms in the proportion 70:30 | |
| Cholesterol | 0.11 g |
| Cholesterol phosphate (sodium salt) | 0.05 g |
| Glycerol | 5.0 g |
| Oxyethylenated sorbitan laurate containing 20 mol of EO, marketed by the company ICI under the name TWEEN 20 ® | 0.17 g |
| Preservatives | 0.3 g |
| Ascorbyl palmitate | 0.01 g |
| Polyethylene glycol (molecular weight = 400) | 1.0 g |
| Propylene glycol | 3.0 g |
| Water | 50.0 g |
| Sodium hyaluronate | 0.1 g |
| Water | 15.0 g |
| Mixture of polyvinylcarboxylic acids marketed by the company Goodrich under the name CARBOPOL 940 ® | 0.25 g |
| Triethanolamine qs | pH 6.5 |
| Demineralized water qs | 100 g |

After decomposition of the sorbitan palmirate and the sorbitan laurate by the enzymes of the skin, this serum makes it possible to treat the skin with palmitic acid, lauric acid, sorbitol, a ceramide and cholesterol, and provides the skin with especially effective protection. Applied daily for 20 days to a tired skin, this serum gives noticeable results.

EXAMPLE 17

Day cream for the face.
A cream having the following formulation is prepared:

| First phase: | |
|---|---|
| Sorbitan palmitate marketed by the company ICI under the name SPAN 40 ® | 1.4 g |
| Wheatgerm glycoceramides marketed by the company ARD | 1.4 g |
| Cholesterol | 0.90 g |
| Cholesterol sulphate (sodium salt) | 0.30 g |
| Glycerol | 4.0 g |
| Demineralized water qs | 56 g |
| Second phase | |
| Volatile silicone oil | 10.0 g |
| Apricot-kernel oil | 10.0 g |
| Mixture of polyvinylcarboxylic acids marketed by the company Goodrich under the name CARBOPOL 940 ® | 0.42 g |
| Methyl para-hydroxybenzoate | 0.20 g |
| Triethanolamine qs | pH 6.5 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 18

Perfumed body milk.

A milk having the following formulation is prepared:

| First phase: | |
|---|---|
| Diglyceryl isostearate marketed by the company Solvay | 0.9 g |
| N-Stearoylglutamic acid monosodium salt marketed by the company Ajinomoto under the name ACYLGLUTAMATE HS 11 ® | 0.1 g |
| Glycerol | 3.0 g |
| Preservatives | 0.3 g |
| Demineralized water qs | 69.7 g |
| Second phase: | |
| Bergamot oil (free from bergapten) | 5.0 g |
| Mixture of polyvinlycarboxylic acids marketed by the company Goodrich under the name CARBOPOL 940 ® | 0.10 g |
| Triethanolamine qs | pH 6 |
| Demineralized water qs | 100 g |

Applied once a day to the body on subjects having firm skin, this milk gives an improvement in the appearance and radiance of the skin, which becomes noticeably more hydrated and smoother after 20 days of application.

EXAMPLE 19

Day cream for the face intended for the nourishment of lacklustre skin.

A cream having the following formulation is prepared:

| First phase: | |
|---|---|
| PEG 400 ® polyethylene glycol stearate produced by biotechnology, marketed by the company Unichema | 1.9 g |
| Cholesterol | 1.9 g |
| N-Stearoylglutamic acid monosodium salt marketed by the company Ajinomoto under the name ACYLGLUTAMATE HS 11 ® | 0.2 g |
| Sorbitol | 4.0 g |
| Unstabilized mixture of amino acids, mannitol, vegetable sucrose, marine glycogen and pyrrolidonecarboxylic acid, marketed by "Laboratoires Serobiologiques de Nancy" under the name HYDROSMYL LS 4513 ® | 0.5 g |
| Preservatives | 0.3 g |
| Demineralized water | |
| Second phase: | |
| Grape-pip oil | 8.0 g |
| Sunflower oil | 8.0 g |
| Volatile silicone oil | 4.0 g |
| Perfume | 0.2 g |
| Mixture of polyvinylcarboxylic acids marketed by the company Goodrich under the name CARBOPOL 940 ® | 0.42 g |
| Triethanolamine qs | pH 6 |
| Demineralized water qs | 100 g |

After a week of daily application every morning to the carefully cleansed face, an improvement is seen in the radiance of the skin of the face, which becomes more radiant.

EXAMPLE 20

Hydrating milk for the body

A milk having the following formulation is prepared:

| First phase: | |
|---|---|
| Sucrose distearate marketed by the company CRODA under the name CRODESTA F 50 ® | 1.35 g |
| Cholesterol | 1.35 g |
| N-Stearoylglutamic acid disodium salt marketed by the company Ajinomoto under the name ACYLGLUTAMATE HS 21 ® | 0.30 g |
| Glycerol | 3.0 g |
| Preservatives | 0.30 g |
| Demineralized water | |
| Second phase: | |
| Light liquid paraffin | 6.0 g |
| Sweet almond oil | 4.0 g |
| Perfume | 0.20 g |
| Mixture of polyvinylcarboxylic acids marketed by the company Goodrich under the name CARBOPOL 940 ® | 0.40 g |
| Triethanolamine qs | pH 6.5 |
| Demineralized water qs | 100 g |

Applied once a day to the body on subjects having firm skin, this milk gives an improvement in the appearance and radiance of the skin, which becomes noticeably more hydrated and smoother after 20 days of application.

EXAMPLE 21

Anti-ageing day cream for the face.

A cream having the following formulation is prepared:

| First phase: | |
|---|---|
| Sucrose distearate marketed by the company Grillo under the name GRILLOTEN PSE 141 G ® | 2.70 g |
| Cholesterol | 2.70 g |
| N-Stearoylglutamic acid disodium salt marketed by the company Ajinomoto under the name ACYLGLUTAMATE HS 21 ® | 0.60 g |
| Vitamin E acetate | 0.60 g |
| Glycerol | 3.00 g |
| L-Hydroxyproline | 1.00 g |
| Guanosine | 0.02 g |
| Preservatives | 0.30 g |
| Polyphosphonate marketed by the company Monsanto Chemical under the name of DEQUEST 2046 ® | 0.80 g |
| Lactic hydrolysate marketed by the company "Laboratoires Serobiologiques de Nancy" under the name LACTOLAN LS ® | 5.00 g |
| Demineralized water | 40 g |
| Second phase: | |
| Apricot-kernel oil | 10.0 g |
| Volatile silicone oil | 10.0 g |
| Sunscreen agents | 1.00 g |
| Vitamin F glycerides | 2.00 g |
| Mixture of polyvinylcarboxylic acids marketed by the company Goodrich under the name CARBOPOL 940 ® | 0.50 g |
| Preservatives | 0.20 g |
| Triethanolamine qs | pH 6.5 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 22

Day cream for the face and neck intended for the care of tired skins.

A cream having the following formulation is prepared:

| First phase: | |
|---|---|
| Mixture of sorbitan stearate and sucrose cocoate marketed by the company ICI under the name ARLATONE 2121 ® | 3.60 g |
| Cholesterol | 3.60 g |
| N-Stearoylglutamic acid monosodium salt marketed by the company Ajinomoto under the name ACYLGLUTAMATE HS 11 ® | 0.80 g |
| Glycerol | 3.00 g |
| D-Panthenol | 1.00 g |
| Mixture of amino acids, mannitol, vegetable sucrose, marine glycogen and pyrrolidone-carboxylic acid, marketed by "Laboratoires Serobiologiques de Nancy" under the name HYDROSMYL LS 4513 ® | 0.2 g |
| Guanosine | 0.01 g |
| Polyphosphonate marketed by the company Monsanto Chemical under the name DEQUEST 2046 ® | 0.80 g |
| Lactic hydrolysate marketed by "Laboratoires Serobiologiques de Nancy" under the name LACTOLAN LS ® | 3.00 g |
| Preservatives | 0.30 g |
| Demineralized water | 40 g |
| Second phase: | |
| Macadamia oil | 7.50 g |
| Grape-pip oil | 5.00 g |
| Volatile silicone oil | 5.0 g |
| Sunscreen agents | 1.00 g |
| Perfume | 0.20 g |
| Natural concentrates of tocopherol | 3.00 g |
| Mixture of polyvinylcarboxylic acids marketed by the company Goodrich under the name CARBOPOL 940 ® | 0.42 g |
| Triethanolamine qs | pH 6 |
| Demineralized water qs | 100 g |

After a week of daily application every morning to the carefully cleansed face and neck, an improvement is seen in the appearance and radiance of the skin of the face and neck, which becomes smoother, firmer and more hydrated with a more radiant complexion.

EXAMPLE 23

Anti-ageing fluid for the face.

A fluid having the following formulation is prepared:

| First phase: | |
|---|---|
| Polyethylene glycol 20 distearate marketed by the company Amerchol under the name GLUCAM E 20 DISTEARATE ® | 1.80 g |
| Cholesterol | 1.80 g |
| Phosphatidic acid sodium salt | 0.40 g |
| Vitamin E acetate | 0.20 g |
| Glycerol | 2.00 g |
| L-Hydroxyproline | 1.00 g |
| Guanosine | 0.01 g |
| Aqueous solution of superoxide dismutase, 5,000 units/ml, marketed by the company Pentapharm | 1.00 g |
| Preservatives | 0.30 g |
| Lactic hydrolysate marketed by "Laboratoires Serobiologiques de Nancy" under the name LACTOLAN LS ® | 5.00 g |
| Demineralized water | |

| Second phase: | |
|---|---|
| Grape-pip oil | 4.0 g |
| Volatile silicone oil | 2.0 g |
| Mixture of polyvinylcarboxylic acids marketed by the company Goodrich under the name CARBOPOL 940 ® | 0.20 g |
| L-Lysine monohydrate qs | pH 6.5 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 24

Anti-ageing serum for the face.

A serum having the following formulation is prepared:

| | |
|---|---|
| Polyglyceryl-2 stearate marketed by the company HOESCHT under the name HOSTACERINE DGS ® | 1.30 g |
| Cholesterol | 0.60 g |
| Phosphatidic acid sodium salt | 0.10 g |
| Glycerol | 3.00 g |
| L-Hydroxyproline | 1.00 g |
| D-Panthenol | 1.50 g |
| Guanosine | 0.01 g |
| Preservatives | 0.30 g |
| Polyphosphonate marketed by the company Monsanto Chemical under the name DEQUEST 2046 ® | 0.80 g |
| Lactic hydrolysate marketed by "Laboratoires Serobiologiques de Nancy" under the name LACTOLAN LS ® | 5.00 g |
| Aqueous solution of superoxide dismutase containing 5,000 units/ml, marketed by the company Pentapharm | 1.00 g |
| Mixture of polyvinylcarboxylic acids marketed by the company Goodrich under the name CARBOPOL 940 ® | 0.50 g |
| Triethanolmine qs | pH 6.5 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 25

Perfumed body milk.

A milk having the following formulation is prepared:

| First phase: | |
|---|---|
| Sorbitan isostearate marketed by the comapny Nikko under the name NIKKOL SI 10 R ® | 0.90 g |
| N-Stearoylglutamic acid disodium salt marketed by the company Ajinomoto under the name ACYLGLUTAMATE HS 21 ® | 0.10 g |
| Glycerol | 3.00 g |
| Preservatives | 0.30 g |
| Demineralized water | |
| Second phase: | |
| Bergamot oil (free from bergapten) | 5.0 g |

| Mixture of polyvinylcarboxylic acids marketed by the company Goodrich under the name CARBOPOL 940 ® | 0.10 g |
|---|---|
| Triethanolamine qs | pH 6.5 |
| Demineralized water qs | 100 g |

Applied once a day to the body on subjects having firm skin, this milk gives an improvement in the appearance and radiance of the skin, which becomes noticeably more hydrated and smoother after 20 days of application.

EXAMPLE 26

Day cream for the face.

A cream having the following formulation is prepared:

| First phase: | |
|---|---|
| Sucrose distearate marketed by the company Croda under the name CRODESTA F 160 ® | 2.20 g |
| Cholesterol | 1.40 g |
| Cholesterol sulphate sodium salt | 0.40 g |
| Glycerol | 3.00 g |
| Demineralized water | |
| Second phase: | |
| Grape-pip oil | 7.0 g |
| Sunflower oil | 5.0 g |
| Volatile silicone oil | 4.0 g |
| Sunscreen agents | 1.0 g |
| Mixture of polyvinylcarboxylic acids marketed by the company Goodrich under the name CARBOPOL 940 ® | 0.42 g |
| Triethanolamine qs | pH 6.5 |
| Demineralized water qs | 100 g |

After a week of daily application every morning to the carefully cleansed face, an improvement is seen in the appearance and radiance of the skin of the face, which becomes smoother, firmer and more hydrated with a more radiant complexion.

EXAMPLE 27

Night cream for the face intended for the nourishment of lacklustre skins.

A cream having the following formulation is prepared:

| First phase: | |
|---|---|
| Sucrose distearate marketed by the company Grillo under the name GRILLOTEN PSE 141 G ® | 1.80 g |
| Cholesterol | 1.80 g |
| Milk sphingomyelin | 1.80 g |
| N-Stearoylglutamic acid disodium salt marketed by the company Ajinomoto under the name ACYLGLUTAMATE HS 21 ® | 0.60 g |
| Unstabilized mixture of amino acids, mannitol, vegetable sucrose, marine glycogen and pyrrolidonecarboxylic acid, marketed by "Laboratoires Serobiologiques de Nancy" under the name HYDROSMYL LS 4513 ® | 1.00 g |
| Preservatives | 0.30 g |
| Demineralized water | 40 g |
| Second phase: | |
| Grape-pip oil | 8.00 g |
| Sunflower oil | 4.00 g |
| Volatile silicone oil | 4.00 g |

| Perfume | 0.20 g |
|---|---|
| Mixture of polyvinylcarboxylic acids marketed by the company Goodrich under the name CARBOPOL 940 ® | 0.42 g |
| Triethanolamine qs | pH 6.5 |
| Demineralized water qs | 100 g |

After a week of daily application every night to the carefully cleansed face of a subject having lacklustre skin, an improvement is seen in the radiance of the skin, which becomes smoother, firmer and more hydrated with a more radiant complexion.

EXAMPLE 28

Anti-ageing day cream for the face.

A cream having the following formulation is prepared:

| First phase: | |
|---|---|
| Hexaglyceryl pentastearate marketed by the company Nikko under the name HEXAGLYN 5S ® | 2.70 g |
| Cholesterol | 2.70 g |
| N-Stearoylglutamic acid disodium salt marketed by the company Ajinomoto under the name ACYLGLUTAMATE HS 21 ® | 0.60 g |
| Vitamin E acetate | 0.60 g |
| Glycerol | 3.00 g |
| L-Hydroxyproline | 1.00 g |
| Guanosine | 0.02 g |
| Preservatives | 0.30 g |
| Polyphosphonate marketed by the company Monsanto Chemical under the name DEQUEST 2046 ® | 0.80 g |
| Lactic hydrolysate marketed by "Laboratoires Serobiologiques de Nancy" under the name LACTOLAN LS ® | 5.00 g |
| Demineralized water | 40 g |
| Second phase: | |
| Apricot-kernel oil | 10.0 g |
| Volatile silicone oil | 10.0 g |
| Sunscreen agents | 1.00 g |
| Vitamin F glycerides | 2.00 g |
| Mixture of polyvinylcarboxylic acids marketed by the company Goodrich under the name CARBOPOL 940 ® | 0.50 g |
| Preservatives | 0.20 g |
| Triethanolamine qs | pH 6.5 |
| Demineralized water qs | 100 g |

After a week of daily application every morning to the carefully cleansed face and neck, an improvement is seen in the appearance and radiance of the skin of the face and neck, which becomes smoother, firmer and more hydrated with a more radiant complexion.

EXAMPLE 29

Anti-ageing day cream for the face and neck intended for the care of tired skins.

A cream having the following formulation is prepared:

| First phase: | |
|---|---|
| Decaglyceryl decastearate marketed by the company Nikko under the name DECAGLYN 10S ® | 2.70 g |
| Cholesterol | 2.70 g |

25
-continued

| | |
|---|---|
| N-Stearoylglutamic acid disodium salt marketed by the company Ajinomoto under the name ACYLGLUTAMATE HS 21 ® | 0.60 g |
| Vitamin E acetate | 0.60 g |
| Glycerol | 3.00 g |
| L-Hydroxyproline | 1.00 g |
| Guanosine | 0.02 g |
| Preservatives | 0.30 g |
| Polyphosphonate marketed by the company Monsanto Chemical under the name DEQUEST 2046 ® | 0.80 g |
| Lactic hydrolysate marketed by "Laboratoires Serobiologiques de Nancy" under the name LACTOLAN LS ® | 5.00 g |
| Demineralized water | 40 g |
| Second phase: | |
| Apricot-kernel oil | 10.0 g |
| Volatile silicone oil | 10.0 g |
| Sunscreen agents | 1.00 g |
| Vitamin F glycerides | 2.00 g |
| Mixture of polyvinylcarboxylic acids marketed by the company Goodrich under the name CARBOPOL 940 ® | 0.50 g |
| Preservatives | 0.20 g |
| Triethanolamine qs | pH 6.5 |
| Demineralized water qs | 100 g |

After a week of daily application every morning to the carefully cleansed face and neck, an improvement is seen in the appearance and radiance of the skin of the face and neck, which becomes smoother, firmer and more hydrated with a more radiant complexion.

EXAMPLE 30

Day cream for the face.

A cream having the following formulation is prepared as in Example 8:

| | |
|---|---|
| First phase: | |
| Sorbitan palmitate marketed by the company ICI under the name SPAN 40® | 3.8 g |
| Cholesterol | 3.8 g |
| α-Sulphone ester of formula | |
| $C_{16}H_{33}-CH\diagup_{SO_3Na}^{COO-(CH_2-CH_2-O)_{\frac{1}{2}}CH_3}$ | 0.4 g |
| Demineralized water qs | 50 g |
| Preservatives | 0.3 g |
| Glycerol | 5.0 g |
| Second phase: | |
| Macadamia oil | 16.0 g |
| Perfume | 0.2 g |
| Mixture of polyvinylcarboxylic acids marketed by the company Goodrich under the name CARBOPOL 940® | 0.42 g |
| Triethanol qs | pH 6 |
| Demineralized water qs | 100 g |

The two formulations defined above are mixed as described in Example 8 to obtain the composition according to the invention.

After a week of daily application every morning to the carefully cleansed face, an improvement is seen in the appearance of the skin of the face, which becomes smoother, firmer and more hydrated.

EXAMPLE 31

A make-up foundation having the following composition is prepared:

| | |
|---|---|
| Phase A: | |
| Sorbitan palmitate marketed by the company ICI under the trade name SPAN 40 ® | 2.85 g |
| Cholesterol | 2.85 g |
| Monosodium glutamate marketed by the company Ajinomoto under the trade name ACYLGLUTAMATE HS 11 ® | 0.3 g |
| Vitamin E acetate | 0.3 g |
| Demineralized water | 35 g |
| Glycerol | 3 g |
| Preservative | 0.1 g |
| Citric acid, 1 H$_2$O | 0.02 g |
| Phase B | |
| Isostearyl neopentanoate sold by the company Van Dyk under the trade name CERAPHIL 375 ® | 5 g |
| Polyphenylmethylsiloxane sold by the company Dow Corning under the trade name DC 556 FLUID COSMETIC ® | 20 g |
| Preservative | 0.15 g |
| Phase C | |
| Yellow iron oxide coated with perfluoro-alkyl phosphate (95:5), sold by the company Wackherr under the trade name COVAFLUOR ® | 0.69 g |
| Brown iron oxide coated with perfluoro-alkyl phosphate (95:5), sold by the company Wackherr under the trade name COVAFLUOR ® | 0.3 g |
| Black iron oxide coated with perfluoro-alkyl phosphate (95:5), sold by the company Wackherr under the trade name COVAFLUOR ® | 0.13 g |
| Titanium dioxide coated with perfluoro-alkyl phosphate (95:5), sold by the company Wackherr under the trade name COVAFLUOR ® | 5.88 g |
| Phase D | |
| Preservative | 0.3 g |
| Demineralized water | 1 g |
| Phase E | |
| Silica microspheres (average diameter: from 1 to 16 μm) | 2 g |
| Phase F | |
| Ethylenediaminetetraacetic acid disodium salt, 2 H$_2$O | 0.05 g |
| Vinylcarboxylic polymer synthesized in an ethyl acetate/cyclohexane mixture, sold by the company Gooddrich under the trade name CARBOPOL 950 ® | 0.4 g |
| Preservative | 0.1 g |
| Sodium hydroxide | 0.108 g |
| Demineralized water | 19.472 g |

The procedure consists in adding the pigments (phase C) to ⅓ of the mixture (vesicular dispersion+oils) (phases A and B), the dispersion being produced beforehand in a conventional manner using a high pressure homogenizer. The whole is mixed for 1 h 30 min, and the remainder of the vesicular dispersion (phase A), the preservatives (phase D), the fillers (phase E) and the neutralized gel (Phase F) are then added successively, homogenizing for 5 min after each introduction.

A natural-beige make-up foundation is thereby obtained. After a week of daily application every morning to the carefully cleansed face, an improvement is seen in the appearance of the skin of the face, which becomes smoother, firmer and more hydrated.

It was found that, in the creams, milks or sera of Examples 8 to 31, the lipid vesicles remained stable after 3 months of storage.

We claim:

1. A process for imparting hydrolysis stability to vesicles dispersed in an aqueous phase, said vesicles comprising a membrane of a lipid phase encapsulating an aqueous phase, said vesicles being prepared from a lipid phase, said process comprising combining a nonionic amphiphilic lipid mixture with at least one ionic amphiphilic lipid in an amount sufficient to impart to said aqueous phase a pH ranging from 5.5 to 7.5 said nonionic amphiphilic lipid mixture being a mixture of esters of at least one polyol and a fatty acid, said at least one polyol being selected from the group consisting of polyethylene glycol containing 1 to 60 ethylene oxide units, sorbitan, sorbitan containing 2 to 60 ethylene oxide units, glycerol containing 2 to 30 ethylene oxide units, a polyglycerol containing 2 to 15 glycerol units, sucrose, and glucose containing 2 to 30 ethylene oxide units, and said fatty acid being a fatty acid containing a saturated or unsaturated, linear or branched $C_5$–$C_{17}$ alkyl chain, the number of alkyl chains per polyol group ranging from 1 to 10; and said ionic amphiphilic lipid being selected from the group consisting of an alkali metal salt of dicetyl phosphate, an alkali metal salt of dimyristyl phosphate, and alkali metal salt of cholesterol sulphate, an alkali metal salt of cholesterol phosphate, monosodium acyl glutamate, disodium acyglutamate, a phospholipid and an alkyl sulphonic compound having the formula:

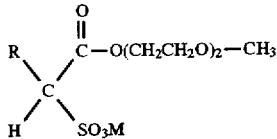

wherein R represents $C_{16}H_{33}$ or $C_{18}H_{37}$ and M represents an alkali metal, or a mixture thereof;

the weight ratio of said nonionic amphiphilic lipid to said ionic amphiphilic lipid in said lipid phase being between 50:1 and 50:25.

2. The process of claim 1 wherein said membrane of a lipid phase of said vesicles contains at least one additive selected from the group consisting of a sterol, a long chain alcohol, a long chain diol and a long chain amine.

3. The process of claim 2 wherein said sterol is cholesterol.

4. The process of claim 1 wherein said vesicles contain at least one active agent having cosmetic or dermopharmaceutic activity, or both.

5. The process of claim 4 wherein said active agent is a water-soluble active agent which is present in said aqueous phase encapsulated in said vesicles.

6. The process of claim 4 wherein said active agent is a fat-soluble active agent and is present in said lipid phase constituting said membrane of said vesicles.

7. The process of claim 6 wherein said fat-soluble active agent is selected from the group consisting of a spingomyeline, a glycoceramide, a natural ceramide and a synthetic ceramide.

8. The process of claim 1 wherein said membrane of a lipid phase of said vesicles contains a mixture of cholesterol and a natural or synthetic ceramide.

9. The process of claim 4 wherein said vesicles contain an amphiphilic active agent distributed between said lipid phase and said aqueous phase encapsulated in said vesicles.

10. The process of claim 1 wherein said aqueous dispersion phase also contains at least one adjuvant selected from the group consisting of a gelling agent, a preservative, a colorant, a pigment, a filler, an opacifier and a perfume.

11. The process of claim 10 wherein said pigment is coated with a silicone, a fluorinated compound selected from the group consisting of a perfluoroalkyl phosphate and a polytetrafluoroethylene or an amino acid.

12. The process of claim 10 wherein said pigment is an iron oxide or a titanium oxide.

13. The process of claim 10 wherein said filler is selected from the group consisting of talc, mica, starch powder, nylon powder and silica powder.

* * * * *